United States Patent
Rauker et al.

(10) Patent No.: US 8,419,695 B2
(45) Date of Patent: Apr. 16, 2013

(54) APPARATUS AND METHOD OF MAINTAINING INSUFFLATION

(75) Inventors: Robert M. Rauker, Chester Springs, PA (US); Robert F. Rioux, Ashland, MA (US); Kristian DiMatteo, Waltham, MA (US); Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1223 days.

(21) Appl. No.: 11/135,428

(22) Filed: May 24, 2005

(65) Prior Publication Data
US 2006/0271095 A1 Nov. 30, 2006

(51) Int. Cl.
*A61M 31/00* (2006.01)

(52) U.S. Cl.
USPC .......................................................... 604/277

(58) Field of Classification Search .................. 604/174, 604/177–180, 275, 277, 278, 523, 104–106, 604/167.06, 164.01, 0.03, 0.06, 170.01–170.03, 604/268, 536, 103.08, 164.03, 164.06, 45, 604/517
See application file for complete search history.

(56) References Cited

U.S. PATENT DOCUMENTS

| | | | |
|---|---|---|---|
| 2,148,541 A | | 2/1939 | Dierker |
| 2,922,415 A | | 1/1960 | Campagna |
| 3,154,077 A | * | 10/1964 | Cannon .......................... 606/192 |
| 3,459,175 A | * | 8/1969 | Miller ............................ 600/431 |
| 3,509,884 A | * | 5/1970 | Bell ........................... 604/101.05 |
| 3,885,567 A | | 5/1975 | Ross |
| 4,776,845 A | * | 10/1988 | Davis ....................... 604/103.03 |
| 4,957,486 A | | 9/1990 | Davis |
| 5,025,778 A | | 6/1991 | Silverstein et al. |
| 5,178,611 A | * | 1/1993 | Rosenberg ..................... 604/172 |
| 5,445,615 A | * | 8/1995 | Yoon ........................... 604/99.04 |
| 5,512,045 A | | 4/1996 | Gurchumelidze |
| 5,569,216 A | | 10/1996 | Kim |
| 5,609,583 A | | 3/1997 | Hakki et al. |
| 5,632,761 A | * | 5/1997 | Smith et al. ................... 606/192 |

(Continued)

FOREIGN PATENT DOCUMENTS

| | | |
|---|---|---|
| WO | WO 00/35529 A1 | 6/2000 |
| WO | WO 2005/009292 A | 2/2005 |

OTHER PUBLICATIONS

International Search Report dated Jun. 27, 2006, for International Application No. PCT/US2006/007649, 4 pages.
U.S. Appl. No. 60/555,356, filed Mar. 23, 2004, McWeeney.
Vining, D. J., et al., "Virtual Colonoscopy," (abstract), Radiology Scientific Program, 1994, vol. 193(P), p. 446.

(Continued)

*Primary Examiner* — Kevin C Sirmons
*Assistant Examiner* — Andrew Gilbert
(74) *Attorney, Agent, or Firm* — Bookoff McAndrews, PLLC

(57) ABSTRACT

An apparatus includes a body configured to be at least partially inserted into a rectum of a patient. The body defines a first passageway and a second passageway between a proximal end portion and a distal end portion. The first passageway is configured to receive a medical tool and the second passageway is configured to communicate an insufflation medium. An insufflation port is coupled to the second passageway and is configured to communicate the insufflation medium to the second passageway. A retention portion is coupled to the body and is configured to have a dimension transverse to an axis defined by the body sufficient to retain at least a portion of the body in the rectum. The retention portion is configured to be located beyond an anus of the patient.

23 Claims, 15 Drawing Sheets

U.S. PATENT DOCUMENTS

| | | | |
|---|---|---|---|
| 5,860,426 A | | 1/1999 | Kleiman |
| 5,947,988 A | | 9/1999 | Smith |
| 5,951,588 A | * | 9/1999 | Moenning ............... 606/213 |
| 6,086,603 A | * | 7/2000 | Termin et al. ............ 606/191 |
| 6,264,631 B1 | * | 7/2001 | Willis et al. ............ 604/103.06 |
| 6,503,192 B1 | | 1/2003 | Ouchi |
| 8,033,995 B2 | * | 10/2011 | Cropper et al. ............ 600/207 |
| 2001/0025134 A1 | | 9/2001 | Bon et al. |

OTHER PUBLICATIONS

Vining, D. J., et al., "Virtual Colonoscopy using Helical CT Scanning, 3-D Reconstruction, and Virtual Reality Image Processing," (abstract), The American Journal of Gastroenterology, Sep. 1994, vol. 89, No. 9, p. 1691.

* cited by examiner

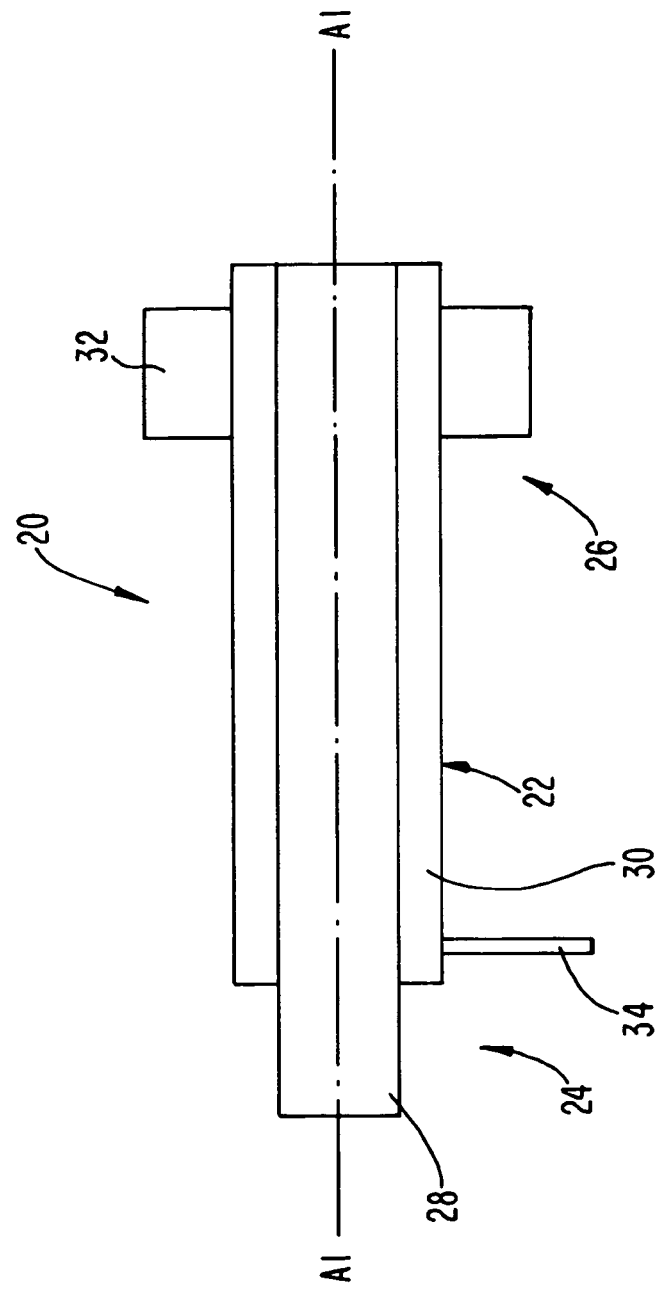

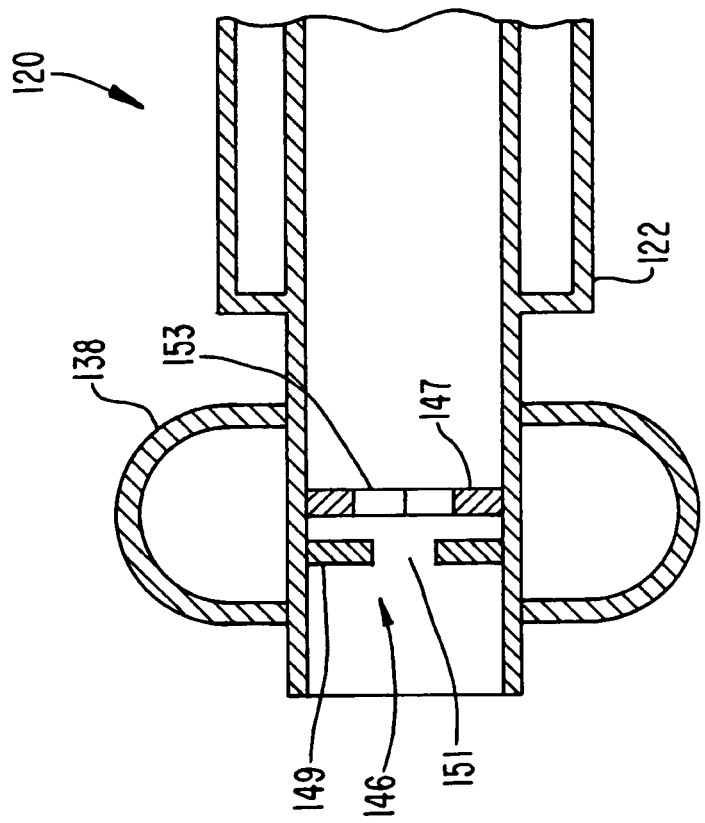
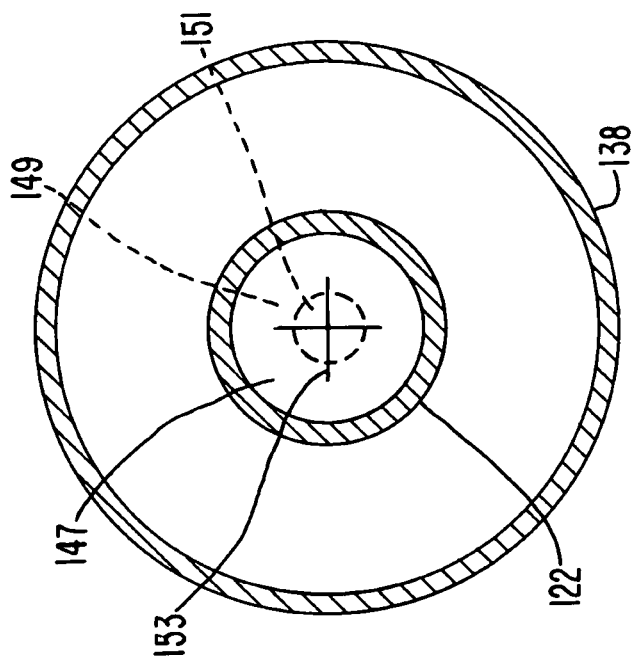
FIG. 4C
FIG. 4D

APPARATUS AND METHOD OF MAINTAINING INSUFFLATION

BACKGROUND

The present invention relates generally to medical devices for use in conjunction with a virtual colonoscopy procedure, and more particularly to an apparatus and method of maintaining insufflation in a colon during a virtual colonoscopy procedure.

Colorectal cancer is one of the leading causes of deaths from malignancy in the United States, with only lung cancer causing more deaths annually. Colon cancer can be prevented because it usually begins as a benign polyp that grows slowly for several years before becoming cancerous. If polyps are detected and removed, the risk of developing colon cancer is significantly reduced.

Unfortunately, widespread colorectal screening and preventive efforts are hampered by several practical impediments, including limited resources, methodologic inadequacies, and poor patient acceptance leading to poor compliance. Moreover, some tests, such as the fecal occult blood test (FOBT) fail to detect the majority of cancers and pre-cancerous polyps. Additionally, since a sigmoidoscopy only examines a portion of the colon, it also misses many polyps that occur in the remainder of the colon. The accuracy of other tests, such as the barium enema, vary and are not always reliable.

A technique for detecting colorectal cancer using helical computed tomography (CT) to create computer simulated intraluminal flights through the colon was proposed as a novel approach for detecting colorectal neoplasms by Vining D J, Shifrin R Y, Grishaw E K, Liu K, Gelfand D W, *Virtual colonoscopy* (Abst), Radiology Scientific Prgm 1994; 193 (P):446. This technique was first described by Vining et al. in an earlier abstract by Vining D J, Gelfand D W, Noninvasive colonoscopy using helical CT scanning, 3D reconstruction, and virtual reality (Abst), SGR Scientific Program, 1994. This technique, referred to as "*virtual colonoscopy*", requires a cleansed colon insufflated with air, a helical CT scan of approximately 30 seconds, and specialized three-dimensional (3D) imaging software to extract and display the mucosal surface. The resulting endoluminal images generated by the CT scan are displayed to a medical practitioner for diagnostic purposes.

There have been several advances in virtual colonoscopy that have improved the imaging techniques, making it a more viable and effective screening option. One advantage of using a virtual colonoscopy as a screening process is the reduction of the invasiveness of a traditional colonoscopy. Traditional colonoscopies are preformed using a colonoscope that has a relatively large diameter (i.e., sufficient to form a seal with the anus) that includes, among other instruments, a scope, multiple lumens for introducing gas and/or liquid, and a working channel for introducing a snare or similar device into the colon. With such a device, there is a risk of straightening and/or perforating the colon because of its relative inflexibility and size.

Another advantage of the virtual colonoscopy procedure is the elimination of the preparation process associated with a traditional colonoscopy. The typical preparation process involves the use of strong laxatives to purge any fecal waste from the colon. Such a process is extremely uncomfortable and is often cited as one of the least desirable parts of the whole procedure. Complete purging is not necessary with the virtual colonoscopy procedure. Rather, a fecal contrasting agent is used to facilitate digital subtraction of any residual feces from the virtual image.

Even though the virtual colonoscopy is largely non-invasive as a screening process, a need still exists for non-invasive and minimally invasive devices and methods for treating the colon (e.g., removing polyps) in the event the virtual colonoscopy identifies a problem area within the colon.

As stated above, traditional colonoscopies are performed using a colonoscope having a relatively large diameter, limited flexibility and typically including multiple instruments, such as a passageway to insufflate the colon, a scope and a working tool. Due to the risks associated with such a device, such as straightening and/or perforating the colon, there is a need for other instrument options that will perform the necessary colonoscopy functions, using a less invasive instrument. Thus, there is a need for a device that provides a conduit for insufflation of the colon by means other than the colonoscope during a colonoscopy procedure being performed in conjunction with a virtual colonoscopy.

SUMMARY OF THE INVENTION

An apparatus includes a body configured to be at least partially inserted into a rectum of a patient. The body defines a first passageway and a second passageway between a proximal end portion and a distal end portion. The first passageway is configured to receive a medical tool and the second passageway is configured to communicate an insufflation medium. An insufflation port is coupled to the second passageway and is configured to communicate the insufflation medium to the second passageway. A retention portion is coupled to the body and is configured to have a dimension transverse to an axis defined by the body sufficient to retain at least a portion of the body in the rectum. The retention portion is configured to be located beyond an anus of the patient.

BRIEF DESCRIPTION OF THE DRAWINGS

The present invention is described with reference to the accompanying drawings. In the drawings, like reference numbers indicate identical or functionally similar elements.

FIG. 3 is a side cross-sectional view of a schematic of an apparatus according to an embodiment of the invention.

FIG. 4C is a side cross-sectional view of a portion of the apparatus shown in FIG. 4 illustrating an alternative sealing portion.

FIG. 4D is a sectional view taken along line 4B-4B in FIG. 4 illustrating the alternative sealing portion shown in FIG. 4C.

DETAILED DESCRIPTION

An apparatus includes a body configured to be at least partially inserted into a rectum of a patient. The body defines a first passageway and a second passageway between a proximal end portion and a distal end portion. The first passageway is configured to receive a medical tool and the second passageway is configured to communicate an insufflation medium. An insufflation port is coupled to the second passageway and is configured to communicate the insufflation medium to the second passageway. A retention portion is coupled to the body and is configured to have a dimension transverse to an axis defined by the body sufficient to retain at least a portion of the body in the rectum. The retention portion is configured to be located beyond an anus of the patient.

Figure 1:
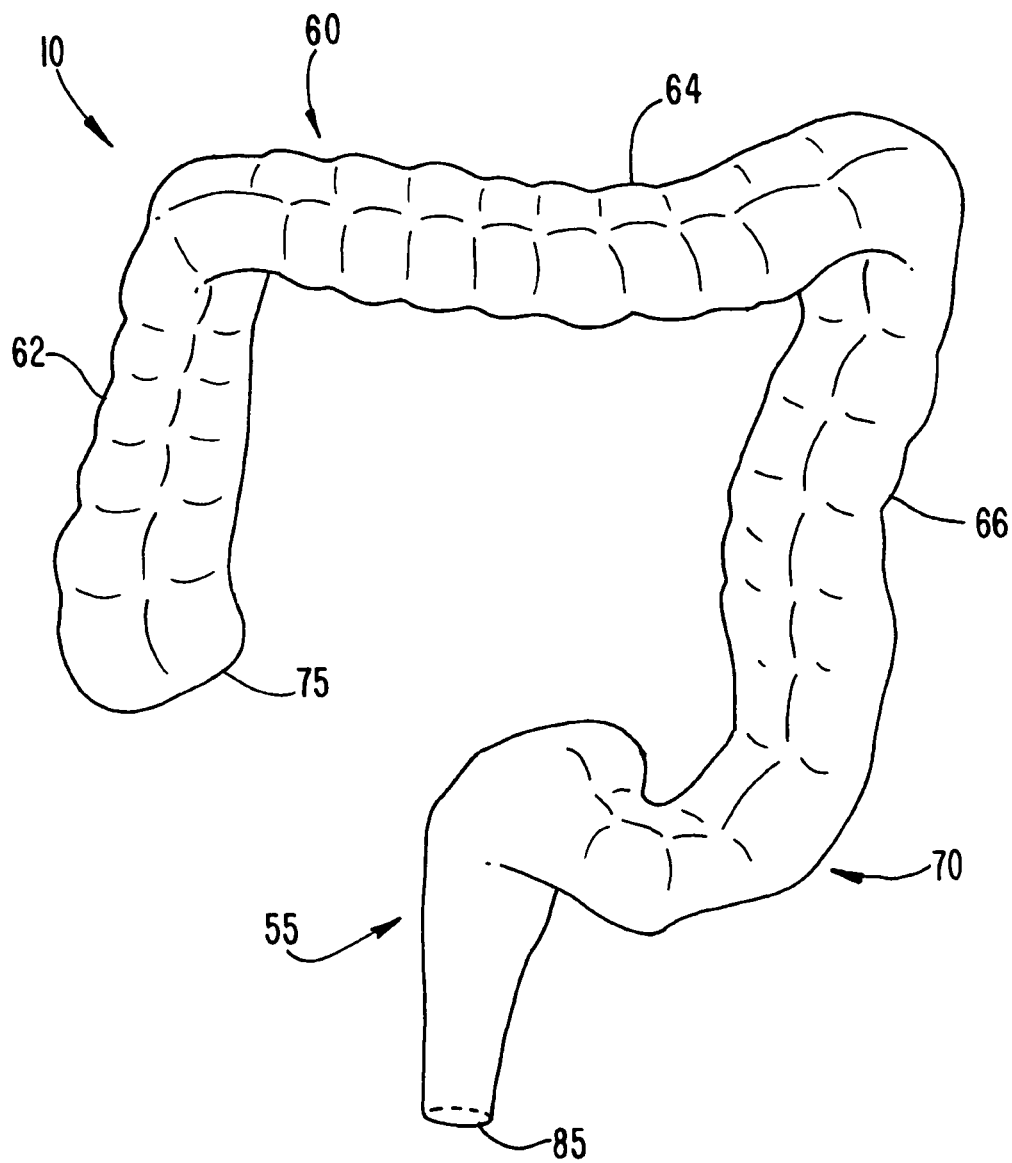
FIG. 1 is an illustration of a large intestine.

Referring to FIG. 1, an illustration of a large intestine (also called the large bowel) 10 is provided by way of background and reference. The colon 60 is the longest part of the large intestine 10, which is a tube-like organ connected to the small intestine (not illustrated) at one end and the anus 85 at the other. The colon 60 and the rectum 55 form the large intestine 10. The colon 60 is the first 4 to 5 feet of the large intestine 10, and the rectum 55 is the last 4 to 5 inches. The part of the colon 60 that joins to the rectum 55 is called the sigmoid colon 70. The junction of the two parts is often referred to as the rectosigmoid colon or rectosigmoid process. The part of the colon 60 that joins to the small intestine is called the cecum 75. The cecum 75 is adjacent the ascending colon 62, which is connected to the transverse colon 64. The transverse colon 64 is connected to the descending colon 66, which is connected to the sigmoid colon 70. The colon 60 removes/absorbs water and some nutrients and electrolytes from partially digested food. The remaining material, solid waste, called stool or feces, moves through the colon 60 to the rectum 55 and leaves the body through the anus 85.

Figure 2A:
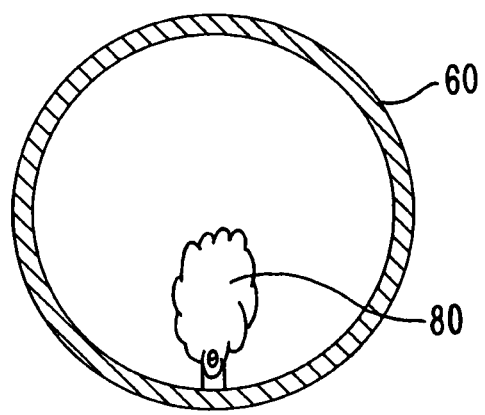
FIGS. 2A and 2B illustrate different types of polyps in a colon.
Figure 2B:
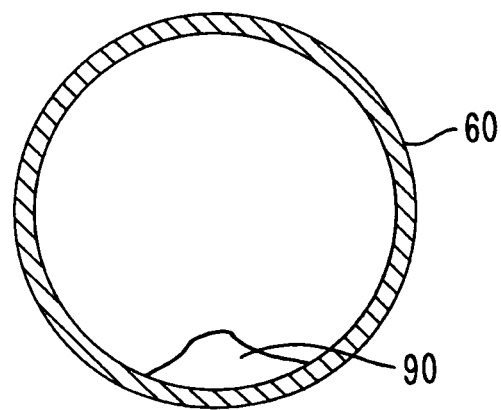

FIGS. 2A-2B illustrate various types of polyps that can form in the colon. A gastrointestinal polyp is a mass of the mucosal surface of the intestine that protrudes into the passageway of the bowel. Polyps can be neoplastic, non-neoplastic, or submucosal. Adenomatous polyps are abnormal growths in the colon and are more likely to develop into or already contain cancer than other types of colon polyps. Adenomatous polyps, however, usually contain tissue that is abnormal but not necessarily cancerous, hence the importance of being able to completely remove a polyp from the colon. The size, type of tissue, and degree of abnormality (mild, moderate, or severe) in a polyp determines the likelihood that it contains cancer.

Some adenomatous polyps are attached to the wall of the colon or rectum by a stalk (a pedunculated polyp 80) as illustrated in FIG. 2A. Some polyps have a broad base with little or no stalk (a sessile polyp 90) as illustrated in FIG. 2B.

FIG. 3 illustrates a schematic side cross-sectional view of an apparatus according to an embodiment of the invention. An apparatus 20 includes a body 22 having a proximal end portion 24 and a distal end portion 26 and defines a first passageway 28 and a second passageway 30, each extending between the proximal end portion 24 and the distal end portion 26. Apparatus 20 also includes a retention portion 32 coupled to the body 22.

First passageway 28 is configured to receive a medical tool, such as a polyp snare, and second passageway 30 is configured to communicate an insufflation medium, such as a gas or a liquid, to the colon of a patient. An insufflation port 34 is coupled to second passageway 30 and is configured to communicate the insufflation medium to second passageway 30. Insufflation port 34 may extend from body 22 or may be formed as an opening in body 22.

Apparatus 20 may become dislodged from the patient's body during use due to internal pressure within the colon of the patient, or through incidental contact by the physician. Because of this concern, retention portion 32 is configured such that in use, it has a dimension transverse to an axis A1 defined by body 22 sufficient to retain at least a portion of the body 22 in the rectum of a patient. The retention portion 32 is also configured to be located beyond the anus of the patient and the distal end portion 26 of the body 22 is configured to extend no further than the rectum of the patient. The retention portion 32 may be constructed with a variety of different materials, such as plastic, rubber, or metal, and may be a variety of different configurations.

For example, in some embodiments, retention portion 32 is an inflatable member. In other embodiments, retention portion 32 is substantially deformable between a constrained configuration, in which it is configured to be inserted through the anus of a patient and an unconstrained configuration, in which it is configured to have a dimension transverse to an axis defined by the body 22 sufficient to retain at least a portion of the body 22 in the rectum of the patient. In another embodiment, retention portion 32 is reconfigurable between a first orientation in which it is configured to be inserted through the anus of a patient, and a second orientation in which it is configured to have a dimension transverse to an axis defined by the body 22 sufficient to retain at least a portion of the body 22 in the rectum of the patient. In other embodiments, apparatus 20 need not include a retention member 32. Examples of some embodiments are discussed in detail below.

Apparatus 20 is configured to be placed in a patient such that it remains positioned within at least a portion of the rectum of a patient during a colonoscopy procedure. One or more medical tools can be inserted through first passageway 28 and into the colon of the patient. During some colonoscopy procedures, an insufflation medium, such as a gas or liquid, is introduced into the colon. Suitable insufflation media include carbon dioxide, saline, and air. The apparatus 20 defines a passageway for the insufflation medium to be communicated into the colon. For example, during a virtual colonoscopy procedure, the apparatus 20 can be positioned in the rectum of the patient and an insufflation medium can be communicated through the second passageway 30 and into the colon of the patient. If the virtual colonoscopy detects an area of interest (e.g., a polyp), a medical tool can be inserted through first passageway 28 and guided to the polyp, or other area of interest. Because the insufflation medium is being provided by a device other than the medical tool, the medical tool (e.g., the polyp snare or endoscope), can be sized much smaller than typically required. In addition, because the polyp or other area of interest is being detected through the use of a virtual colonoscopy, it is not necessary for the medical tool to include an optical scope or catheter with fiber optics, such as the catheter disclosed in U.S. Patent Application No. 60/555, 356 incorporated herein by reference. This further reduces the required size of the medical tool and thus reduces patient discomfort.

Figure 4:
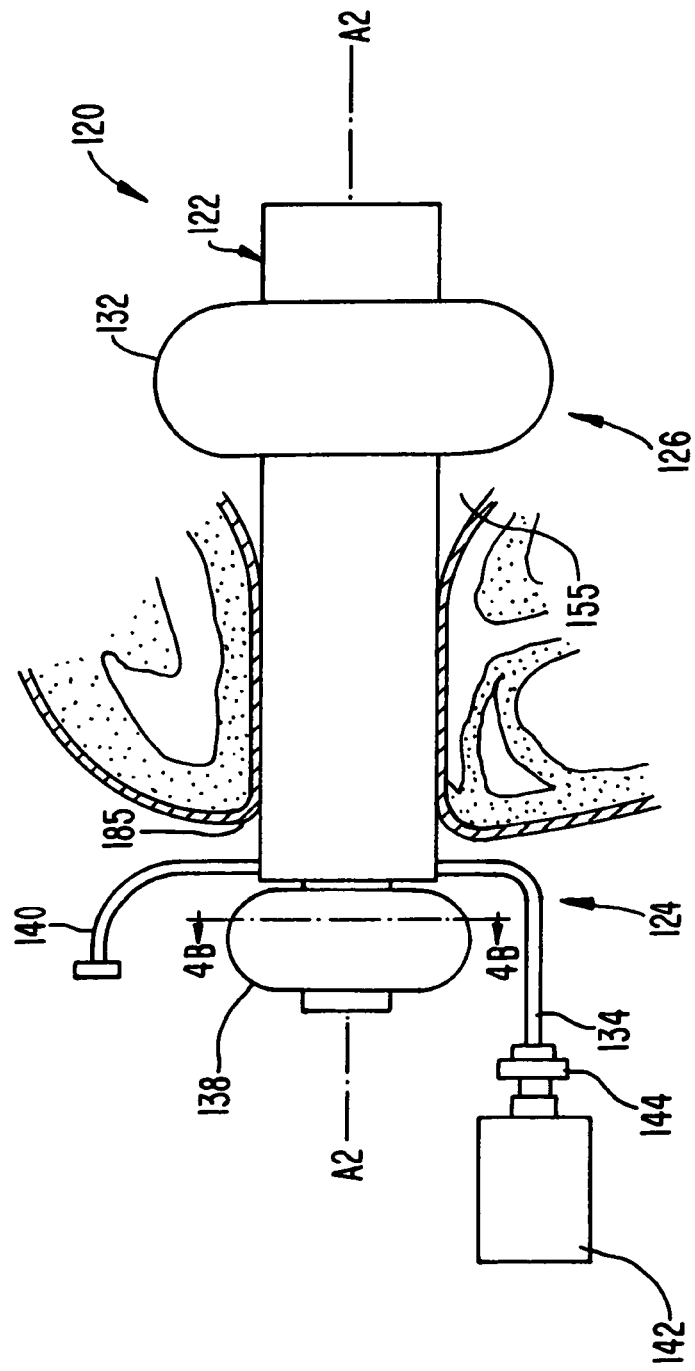
FIG. 4 is a side view of an apparatus according to an embodiment of the invention.
Figure 4A:
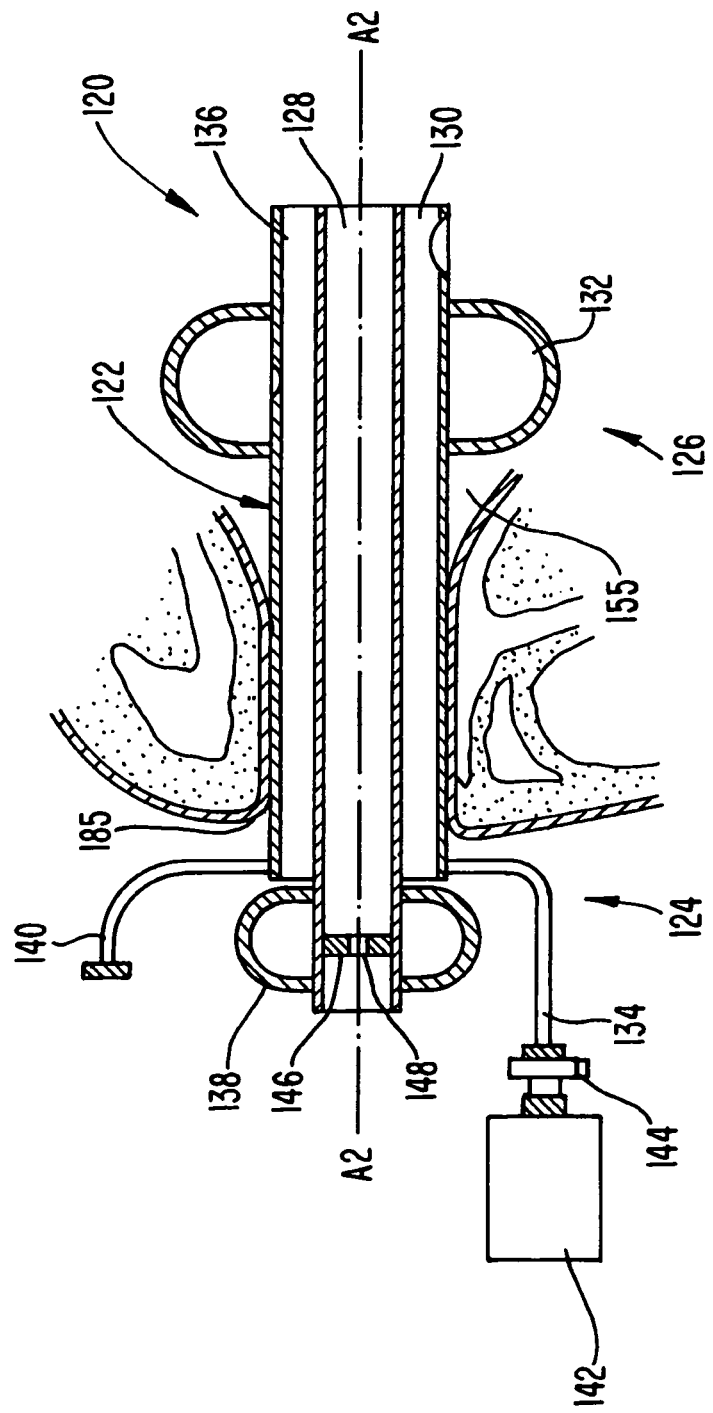
FIG. 4A is a side cross-sectional view of the apparatus shown in FIG. 4.

FIGS. 4 and 4A illustrate an embodiment of an apparatus 120 of the invention positioned within a rectum 155 of a patient. Apparatus 120 includes a body 122 having a proximal end portion 124 and a distal end portion 126, and defining a first passageway 128, a second passageway 130, and a third passageway 136, each extending between the proximal end portion 124 and the distal end portion 126. Apparatus 120 also includes a first retention portion 132 coupled to the body 122 adjacent the distal end portion 126, and a second retention portion 138 coupled to the body 122 adjacent the proximal end portion 124. Body 122 is configured to sealingly engage an anus 185 of the patient. For example, body 122 may be constructed of a material that conforms to the anus of the patient. In addition, body 122 may be dimensioned according to the size of the anus of the patient to accommodate a sealing fit between body 122 and the anus of the patient.

First passageway 128 is configured to receive a medical tool, such as a polyp snare, and second passageway 130 is configured to communicate an insufflation medium, such as a gas or liquid, to the colon of the patient. An insufflation port 134 is coupled to second passageway 130 and is configured to communicate the insufflation medium to second passageway 130. Insufflation port 134 is also coupled to a source of pressurized liquid or gas 142. A pressure relief valve 144 is coupled to the source of pressurized liquid or gas 142 to provide an emergency relief when the pressure of the gas or liquid in the colon exceeds a specified level. Third passageway 136 is coupled to a supply port 140 and is configured to communicate either a gas or liquid to first retention portion 132.

In the illustrated embodiment, first retention portion 132 is an inflatable member, such as a balloon. In its inflated state, first retention portion 132 has a dimension transverse to an axis A2 defined by body 122 sufficient to retain at least a portion of the body 122 in the rectum 155 of the patient. The first retention portion 132 is also configured to be located beyond the anus 185 of the patient as illustrated in FIG. 4A. The first retention portion 132 may be constructed with a variety of different materials, such as rubber, plastic or other suitable material, and be a variety of different shapes.

Figure 4B:
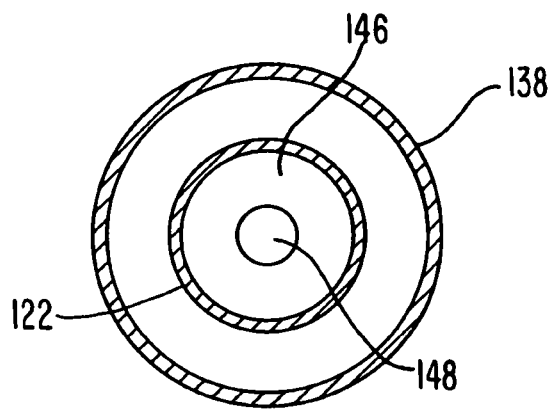
FIG. 4B is a cross-sectional view of the apparatus shown in FIG. 4 taken along line 4B-4B in FIG. 4.

Second retention portion 138 is coupled to body 122 at a location on body 122 positioned outside of the patient during use, as illustrated in FIGS. 4A and 4B. Second retention portion 138 is configured to have a dimension transverse to the axis A2 defined by body 122 sufficient to inhibit displacement of the body 122 into the colon beyond a predetermined location.

The second retention portion 138 may be constructed with a variety of different materials, such as plastic, rubber, metal or other suitable material. Second retention portion 138 can also have a variety of different configurations. For example, in some embodiments, second retention portion 138 is an inflatable member and is coupled to a source of gas or liquid. In some embodiments, the source of gas or fluid can be source 142. In another embodiment, second retention portion 138 is substantially deformable. In another embodiment, second retention portion 138 is a reconfigurable member. Other configurations are possible, as long as they inhibit displacement of body 122 into the colon beyond a predetermined location. In still other embodiments, second retention portion 138 need not be included.

As shown in FIGS. 4A and 4B, body 122 includes a sealing portion 146. Sealing portion 146 is coupled to first passageway 128 and is configured to sealingly receive a medical tool, such as a polyp snare. Sealing portion 146 prevents leakage of the insufflation medium through first passageway 128 when a medical tool is positioned within first passageway 128. Sealing portion 146 is a radially disposed flange that defines a hole 148 through which the medical tool can be inserted. The outer diameter of the medical tool can be sized to match or matingly fit the diameter of the hole 148, such that a seal is created when the medical tool is inserted into hole 148.

Figure 4E:
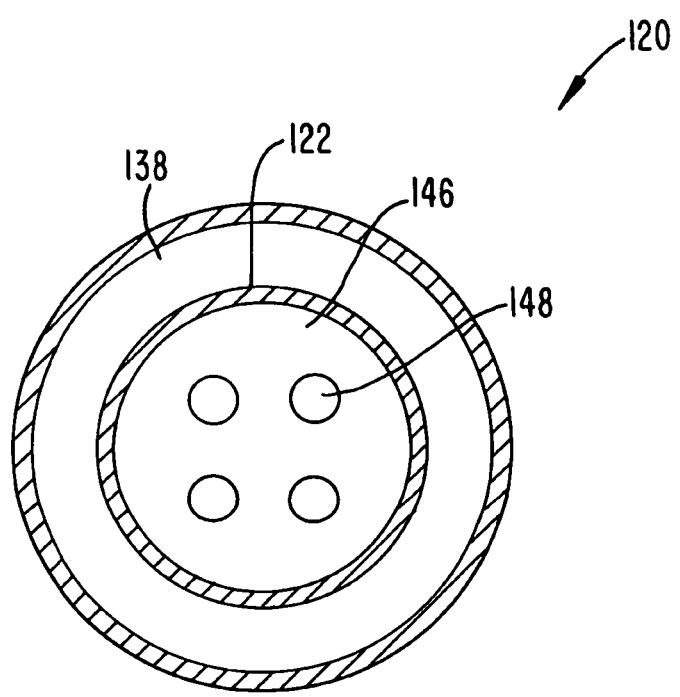
FIG. 4E is a sectional view taken along line 4B-4B in FIG. 4 illustrating another alternative sealing portion.

Alternatively, the sealing portion can include other types of valves to help prevent leakage of the insufflation medium. For example, FIGS. 4C and 4D illustrate one possible type of valve that can be used. The valve shown in FIGS. 4C and 4D includes two components, a first member 147 having a cross-cut surface (slits) 153 and a second member 149 defining a hole 151. In this embodiment, the medical tool can be inserted through the hole 151, and pushed through the cross-cut surface 153. The diameter of hole 151 is smaller than the cross-cut surface 153. In another embodiment, sealing portion 146 can define multiple holes 148 as shown in FIG. 4E, which can accommodate the insertion of multiple medical tools into apparatus 120.

In use, apparatus 120 is inserted through the anus 185 of the patient such that it remains positioned within at least a portion of the rectum 155 of the patient. Gas or liquid is communicated to first retention portion 132 through third passageway 136 to prevent apparatus 120 from being dislodged from its position within at least a portion of the rectum 155 of the patient. An insufflation medium, such as a gas or liquid, can be communicated into the colon through second passageway 130, allowing for insufflation of the colon. A medical tool, such as a polyp snare, can then be inserted through first passageway 128 and into the colon of a patient if necessary.

Figure 5A:
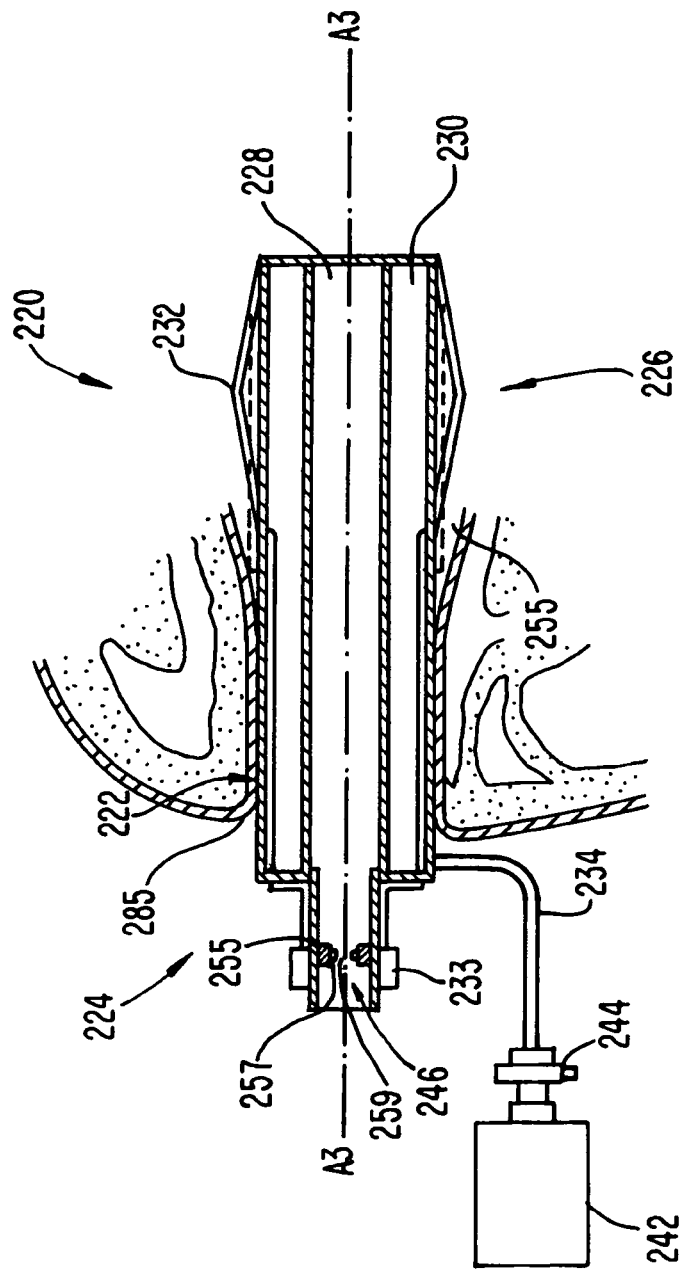
FIG. 5A is a side cross-sectional view of an apparatus according to an embodiment of the invention.

FIG. 5A illustrates another embodiment of an apparatus 220 of the invention positioned at least partially within a rectum 255 of a patient. In the illustrated embodiment, apparatus 220 includes a body 222 having a proximal end portion 224 and a distal end portion 226, and defining a first passageway 228 and a second passageway 230, each extending between the proximal end portion 224 and the distal end portion 226. Apparatus 220 also includes a retention portion 232 coupled to the body 222 adjacent the distal end portion 226. Body 222 is configured to sealingly engage an anus 285 of the patient. For example, body 222 may be constructed of a material that conforms to the anus of the patient. In addition, body 222 may be dimensioned according to the size of the anus of the patient to accommodate a sealing fit between body 222 and the anus 285 of the patient.

First passageway 228 is configured to receive a medical tool, such as a polyp snare, and second passageway 230 is configured to communicate an insufflation medium, such as a gas or liquid, to the colon of the patient. An insufflation port 234 is coupled to second passageway 230 and is configured to communicate the insufflation medium to second passageway 230. Insufflation port 234 is also coupled to a source of pressurized gas or liquid 242, and a pressure relief valve 244 is coupled to the source of pressurized gas or fluid 242 provide an emergency relief when the pressure of the gas or liquid in the colon exceeds a specified level.

In the illustrated embodiment, retention portion 232 is a reconfigurable member, such as a mechanical retainer. Retention portion 232 is reconfigurable between a first orientation, in which it is configured to be inserted through the anus 285 of the patient and a second orientation, in which it is configured to have a dimension transverse to an axis A3 defined by the body 222 sufficient to retain at least a portion of body 222 in the rectum 255 of the patient (i.e., prevent body 222 from being dislodged). Retention portion 232 can be configured such that it assumes the second orientation automatically after insertion into the rectum 255, or may alternatively be configured to require actuation, for example, by a mechanical actuator 233. Retention portion 232 is configured to be located beyond the anus 285 of the patient as illustrated in FIG. 5A. Retention portion 232 may be constructed with a variety of different materials, such as plastic, rubber, metal or other suitable material, and can be a variety of different shapes.

In FIG. 5A, retention portion 232 is slidably coupled to body 222 with a slide mechanism. In a retracted configuration, retention portion 232 is moved into a collapsed position substantially parallel to and adjacent the body 222 to allow for insertion of apparatus 220 through the anus 285 of the patient. In an un-retracted or extended configuration, retention portion 232 is moved such that retention portion 232 bends or flexes away from body 222 a sufficient distance to prevent apparatus 220 from becoming dislodged from the patient's body.

Figure 5B:
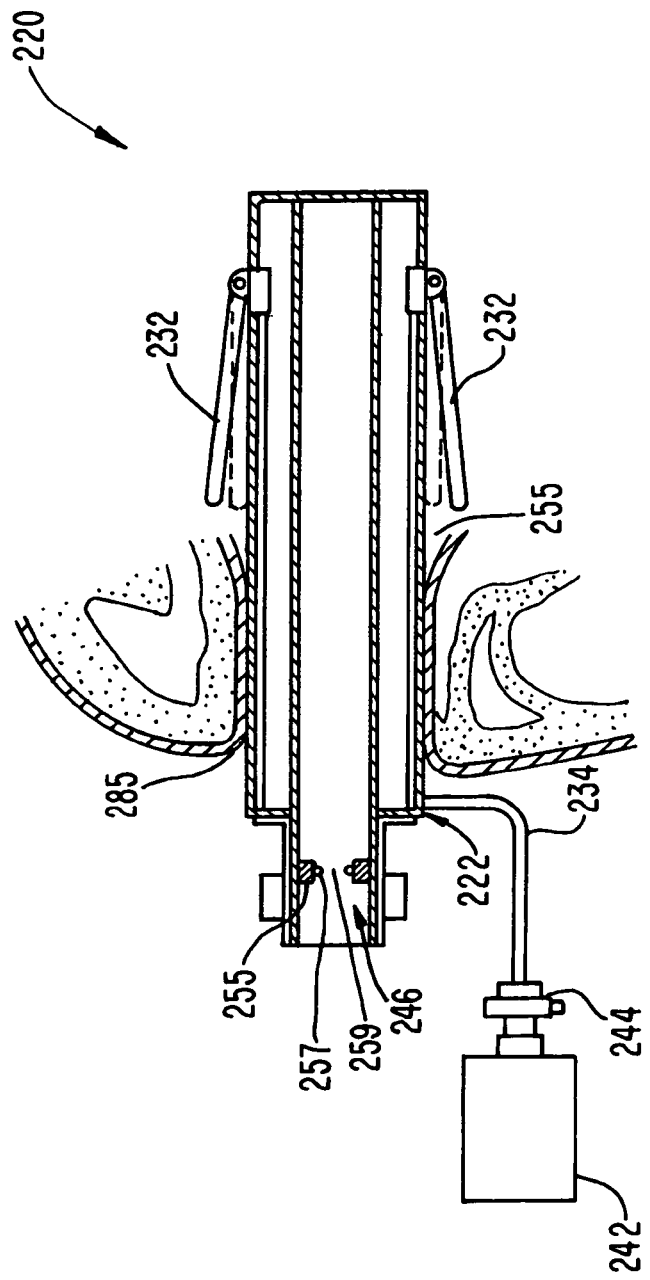
FIG. 5B is a side cross-sectional view of an apparatus according to an embodiment of the invention.

FIG. 5B illustrates an alternative embodiment of retention portion 232. In this embodiment, retention portion 232 is pivotably coupled to body 222 such that in a retracted configuration retention portion 232 is pivoted to a folded position substantially parallel to and adjacent body 222 to allow for insertion of apparatus 220 through the anus 285 of the patient. In an un-retracted or extended configuration, a portion of retention portion 232 is pivoted away from body 222 a sufficient distance to prevent apparatus 220 from becoming dislodged from the patient's body.

Body 222 also includes a sealing portion 246, which in the illustrated embodiment includes a radially disposed flange member 255 and an o-ring 257. Sealing portion 246 is coupled to first passageway 228 and configured to sealingly receive a medical tool through an opening 259 defined by flange member 255 and o-ring 257. The opening 259 may be sized such that the outer diameter of the medical tool matches or matingly fits the opening 259. In alternative embodiments, o-ring 257 may not be included, similar to sealing portion 146. Flange member 255 may be constructed with suitable flexible material such that it sufficiently conforms to the outer diameter of the medical tool to provide a seal.

In use, apparatus 220 is inserted through the anus 285 of the patient with the retention portion 232 in a retracted configuration. Once apparatus 220 is positioned at the desired location within at least a portion of the rectum 255 of the patient, retention portion 232 may assume its extended configuration, either automatically or by external actuation, to help retain apparatus 220 in its position within at least a portion of the rectum 255 of the patient. An insufflation medium can be communicated through second passageway 230 and into the colon of the patient, allowing for insufflation of the colon. A medical tool, such as a polyp snare, can then be inserted through first passageway 228 and into the colon of the patient if necessary. Once the procedure is completed, retention portion 232 is placed back into a retracted configuration to remove apparatus 220 from the patient.

Figure 6A:
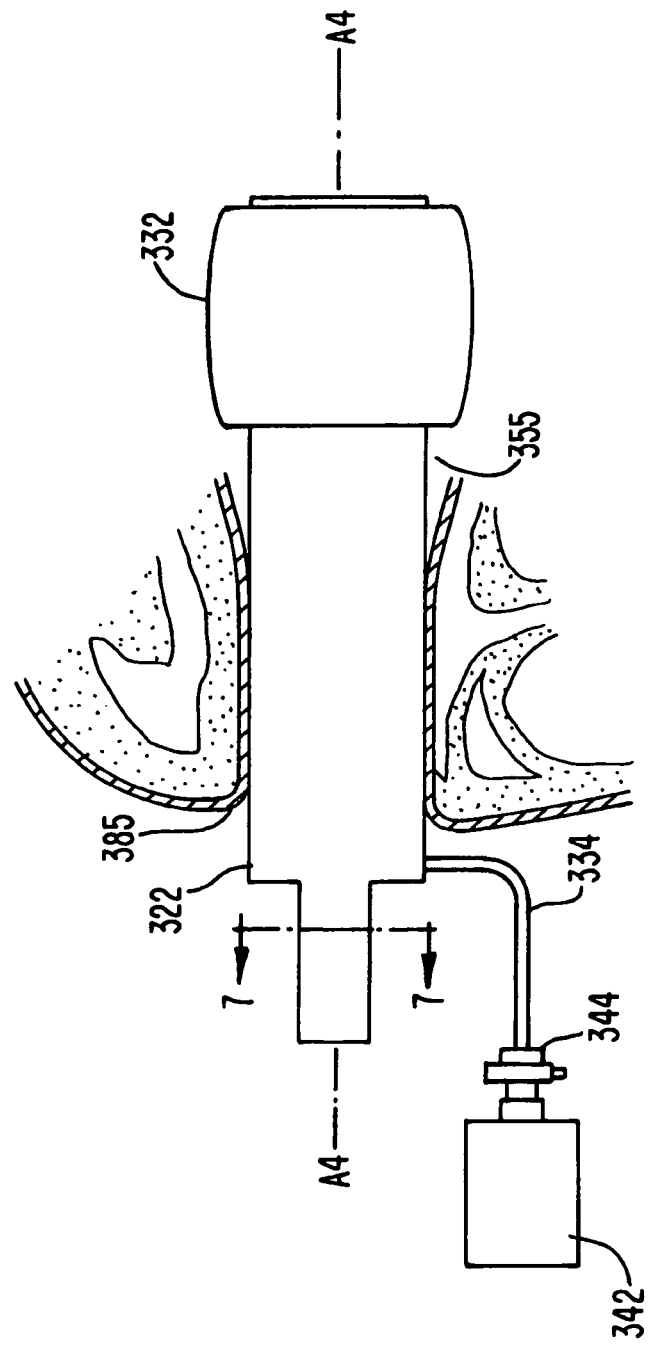
FIG. 6A is a side view of an apparatus according to another embodiment of the invention.
Figure 6B:
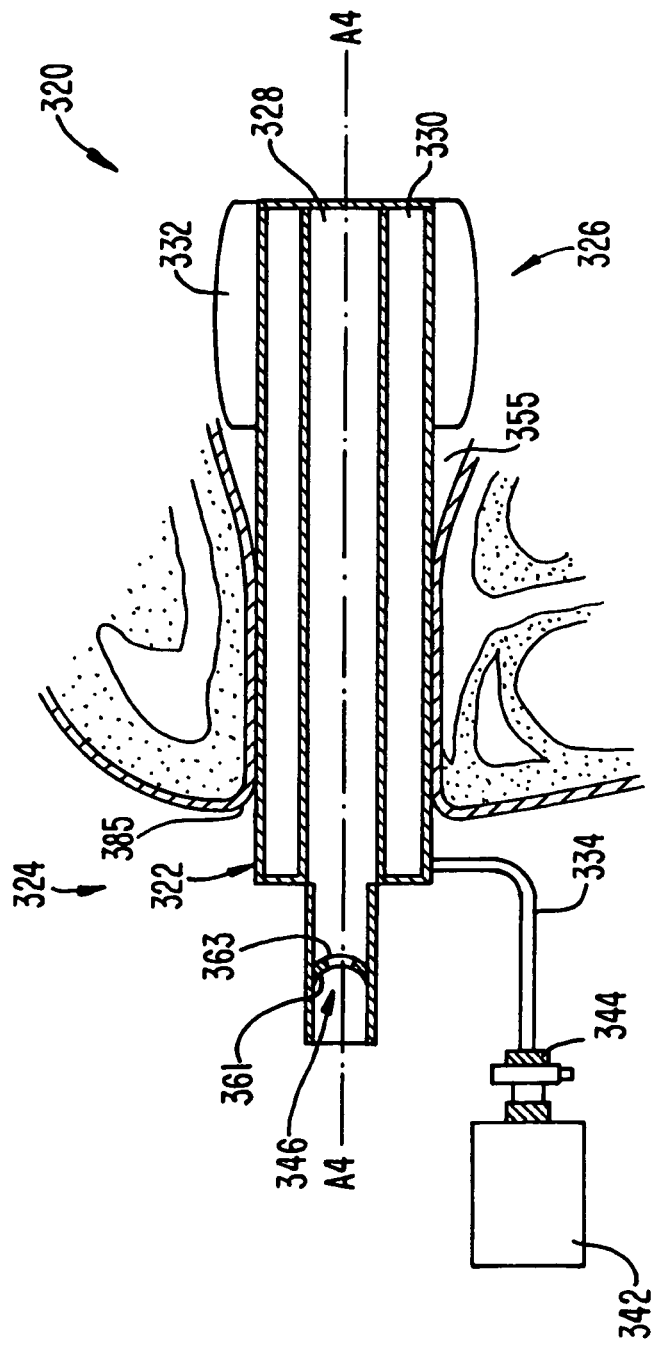
FIG. 6B is a side cross-sectional view of the apparatus shown in FIG. 6A.

FIGS. 6A and 6B illustrate an embodiment of an apparatus 320 of the invention positioned at least partially within a rectum 355 of a patient. Apparatus 320 includes a body 322 having a proximal end portion 324 and a distal end portion 326, and defining a first passageway 328 and a second passageway 330, each extending between the proximal end portion 324 and the distal end portion 326. Apparatus 320 also includes a retention portion 332 coupled to the body 322 adjacent distal end portion 326. Body 322 is configured to sealingly engage an anus of the patient. For example, body 322 may be constructed of a material that conforms to the anus of the patient. In addition, body 322 may be dimensioned according to the size of the anus 385 of the patient to accommodate a sealing fit between body 322 and the anus of the patient.

First passageway 328 is configured to receive a medical tool, such as a polyp snare, and second passageway 330 is configured to communicate an insufflation medium, such as a gas or a liquid, into the colon of the patient. An insufflation port 334 is coupled to second passageway 330 and is configured to communicate the insufflation medium to second passageway 330. Insufflation port 334 is also coupled to a source of pressurized gas or fluid 342, and a pressure relief valve 344 is coupled to the source of pressurized gas or fluid 342 to regulate the pressure of the gas or fluid in the colon.

Retention portion 332 is substantially deformable between a constrained configuration, in which it is configured to be inserted through the anus 385 of the patient and an unconstrained configuration, in which it is configured to have a dimension transverse to an axis A4 defined by the body 322 sufficient to retain at least a portion of the body 322 in the rectum 355 of the patient. Retention portion 332 is also configured to be located beyond the anus 385 of the patient as illustrated in FIGS. 6A and 6B. Retention portion 332 may be constructed with a variety of compressible materials, such as rubber or plastic, and be a variety of different shapes. Retention portion 332 is configured to be compressed, deflected or deformed into the constrained or compressed configuration to allow for apparatus 320 to be inserted through the anus 385 of the patient with a force that is not too uncomfortable to the patient. In the unconstrained configuration (i.e., when retention portion 332 is located within the rectum of the patient) retention portion 332 expands or uncompresses sufficiently to prevent apparatus 320 from being inadvertently removed from the rectum 355 by forces experienced during the procedure (e.g., forces caused by insufflation, fluid pressure, and doctor manipulation).

Figure 7:
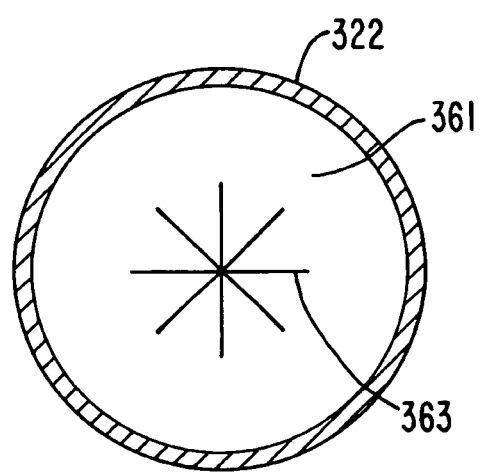
FIG. 7 is a sectional view taken along line 7-7 in FIG. 6.

As shown in FIG. 6B, body 322 includes a sealing portion 346. Sealing portion 346 includes an arched member 361 having a cross-cut surface 363 (slits), as shown in FIG. 7. Sealing portion 346 is coupled to first passageway 328 and is configured to sealingly receive a medical tool through the cross-cut surface 363.

In use, apparatus 320 is pushed or inserted through the anus 385 of the patient such that it is positioned within at least a portion of the rectum 355 of the patient. After insertion, retention portion 332 assumes its uncompressed configuration to hold apparatus 320 in position within at least a portion of the rectum of the patient. An insufflation medium can be communicated through second passageway 336 and into the colon of the patient. A medical tool, such a polyp snare, can then be inserted through first passageway 328 and into the colon of the patient if necessary. Once the procedure is completed, apparatus 320 can be removed from the patient by pulling on apparatus 320 with enough force to compress retention portion 332 sufficiently to allow it to pass back through the anus 385 of the patient.

Figure 8:
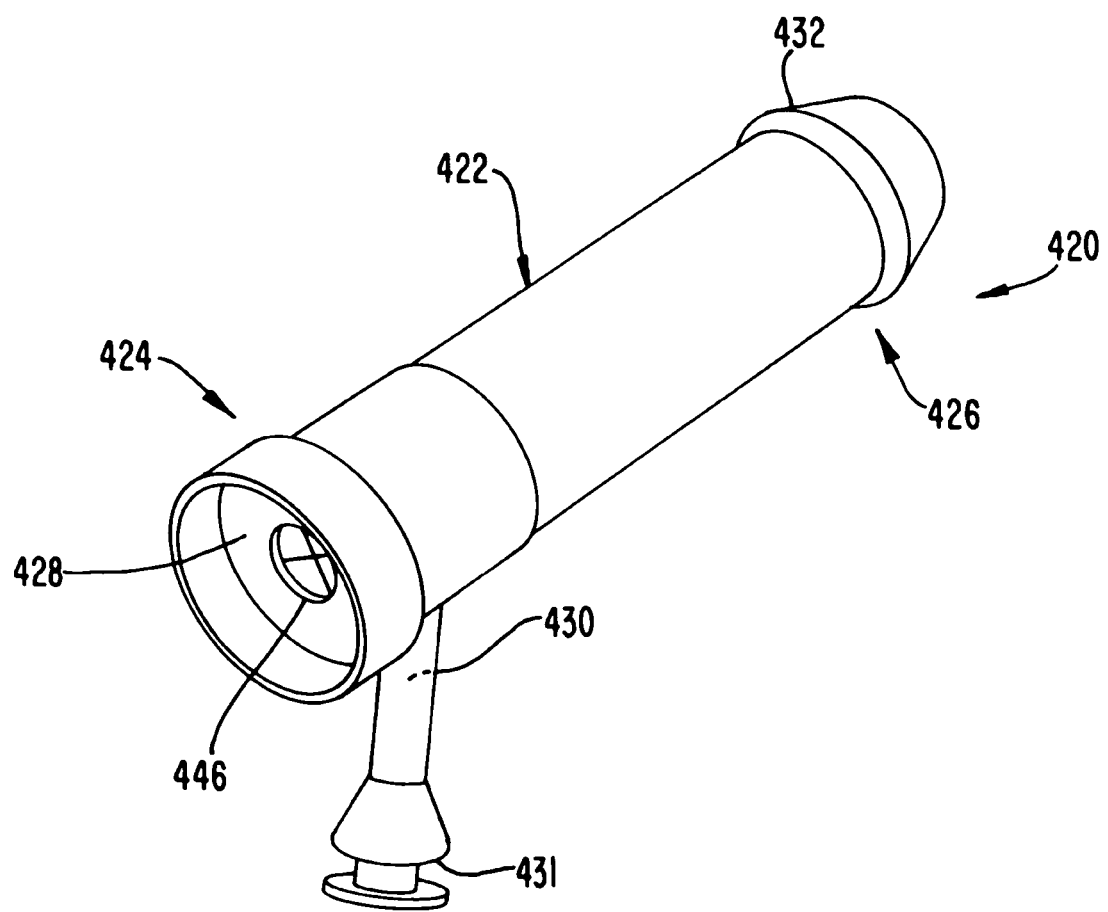
FIG. 8 is a perspective view of an apparatus according to another embodiment of the invention.

FIG. 8 illustrates an apparatus 420 according to another embodiment of the invention. Apparatus 420 includes a body 422 having a proximal end portion 424 and a distal end portion 426, and defining a first passageway 428 and a second passageway 430. This embodiment includes a molded retention portion 432 on the distal end portion 426 of the body 422. The first passageway 428 is configured to receive a medical tool, such as a polyp snare. The second passageway 430 is configured to communicate an insufflation medium to the colon of the patient. In this embodiment the first passageway 428 and the second passageway 430 converge into a single lumen. The apparatus 420 includes a sealing portion 426 similar to the sealing portion illustrated in FIGS. 4C and 4D to prevent leakage of the insufflation medium.

In use, the insufflation gas would be provided through second passageway 430 and then second passageway 430 would be sealed via a valve 431. The medical tool can then be passed through the sealing portion 446 and first passageway 428, and into the colon of the patient.

Figure 9:
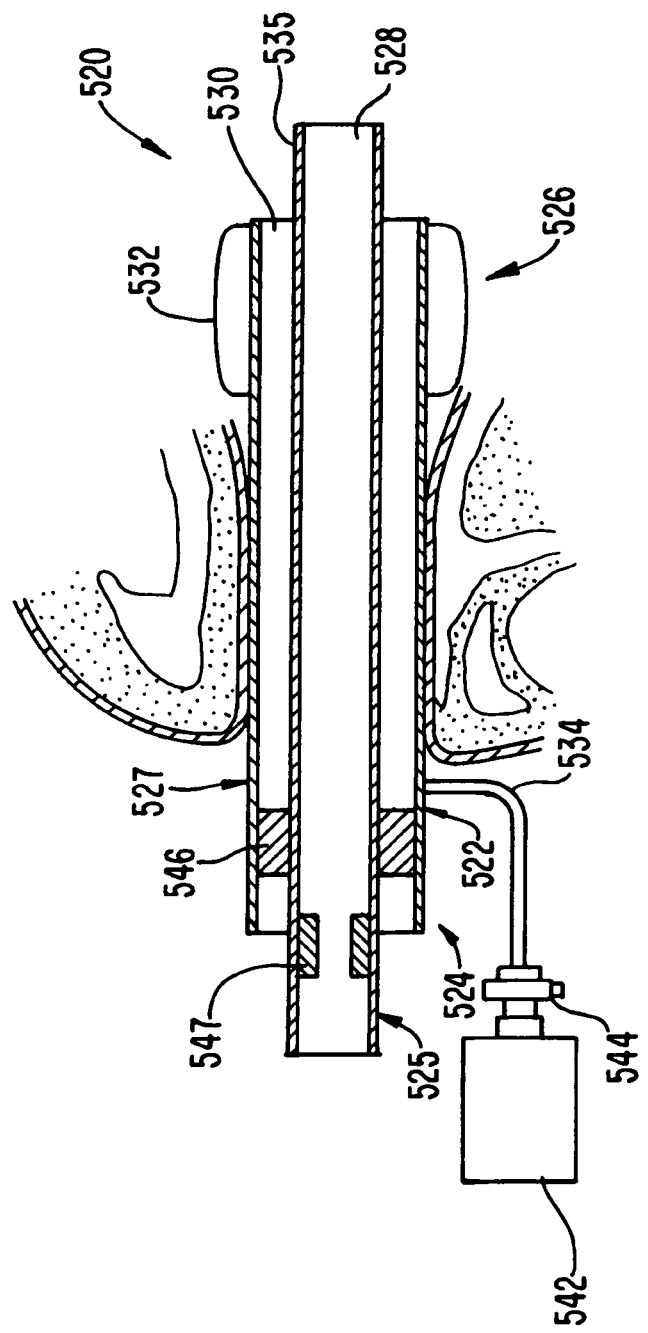
FIG. 9 is a cross-sectional view of another apparatus according to an embodiment of the invention.

FIG. 9 illustrates an apparatus 520 according to another embodiment of the invention. Apparatus 520 includes a body 522 having a proximal end portion 524 and a distal end portion 526. In this embodiment, the body includes a first portion 525 defining a first passageway 528, and a second portion 527 defining a second passageway 530. The first passageway 528 is configured to receive a medical tool, such as a polyp snare, and the second passageway 530 is configured to communicate an insufflation medium to the colon of the patient. The apparatus 520 includes a first sealing portion 546 configured to sealingly receive the first portion 525, and a second sealing portion 547 configured to sealingly receive a medical tool. An insufflation port 534 is coupled to the second passageway 530 on one end and to a source of pressurized liquid or gas 542 on an opposite end. A pressure relief valve 544 is coupled to the source of pressurized liquid or gas 542 to provide an emergency relief when the pressure of the gas or liquid in the colon exceeds a specified level.

CONCLUSION

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents.

The previous description of the embodiments is provided to enable any person skilled in the art to make or use the invention. While the invention has been particularly shown and described with reference to embodiments thereof, it will be understood by those skilled in art that various changes in form and details may be made therein without departing from the spirit and scope of the invention. For example, the various features of apparatus 20 may include other configurations, shapes and materials not specifically illustrated, while still remaining within the scope of the invention.

Further, the particular number of passageways included within apparatus 20 (120, 220, 320, 420, 520) can be varied as well as the particular arrangement of the passageways. For example, the first passageway (28, 128, 228, 328, 428, 528), the second passageway (30, 130, 230, 330, 430, 530) and the third passageway (136) can be arranged concentrically or parallel to each other or in other suitable arrangements. Likewise, multiple passageways for each function can be used rather than one single passageway. Moreover, additional passageways can be included to allow additional functions to be performed with apparatus 20.

What is claimed is:

1. An apparatus, comprising:
a body including a plurality of interior walls configured to be at least partially inserted into a rectum of a patient, said body defining a first passageway, a second passageway, and a third passageway between a proximal end portion and a distal end portion of said body, wherein each of the plurality of interior walls are fixed relative to one another, each of said second and third passageways having a length which extends from a proximal-most end of the body to a distal-most end of the body, said first passageway configured to receive a medical tool, said second passageway configured to communicate an insufflation medium into contact with tissue of a patient, wherein said length of said second passageway and said length of said third passageway extend parallel to said first passageway;
an insufflation port coupled to said second passageway configured to communicate said insufflation medium directly to said second passageway; and
a retention portion coupled to said body, said retention portion configured to have a dimension transverse to an axis defined by said body sufficient to retain at least a portion of said body in the rectum, said retention portion configured to be located in the rectum.

2. The apparatus of claim 1, wherein said retention portion is inflatable.

3. The apparatus of claim 1, wherein said retention portion is substantially deformable between a constrained configuration in which it is configured to be inserted through an anus and an unconstrained configuration in which it is configured to have a dimension transverse to said axis defined by said body sufficient to retain at least a portion of said body in the rectum.

4. The apparatus of claim 1, wherein said retention portion is reconfigurable between a first orientation in which it is configured to be inserted through an anus and a second orientation in which it is configured to have a dimension transverse to said axis defined by said body sufficient to retain at least a portion of said body in the rectum.

5. The apparatus of claim 1, wherein the insufflation medium is a pressurized liquid and further comprising a source of pressurized fluid or gas.

6. The apparatus of claim 5, further comprising a pressure relief valve coupled to said source of pressurized fluid.

7. The apparatus of claim 1, further comprising a seal coupled to said first passageway and configured to sealingly receive a medical tool.

8. The apparatus of claim 1, further comprising a second retention portion coupled to said body and configured to have a dimension transverse to said axis defined by said body sufficient to inhibit displacement of said body into the rectum beyond a predetermined location, said second retention portion coupled to said body outside of the rectum.

9. The apparatus of claim 1, wherein said third passageway is configured to communicate at least one of a fluid or gas to said retention portion.

10. The apparatus of claim 1, wherein said retention portion is expandable.

11. The apparatus of claim 1, wherein said body is formed with a material such that said body conforms to the anus of the patient and provides a sealing fit between said body and the anus of the patient.

12. The apparatus of claim 1, wherein the retention portion is a first retention portion and is coupled to a distal end portion of said body, the apparatus further comprising:
a second retention portion coupled to a proximal end portion of said body, said second retention portion being inflatable and configured to be disposed outside of the patient's body.

13. An apparatus, comprising:
a body configured to be at least partially inserted into a rectum of a patient, said body defining a first passageway and including a plurality of interior walls a second passageway, wherein each of the plurality of interior walls are fixed relative to one another, said first passageway configured to receive a medical tool, said second passageway being circumferential and entirely surrounding said first passageway, said second passageway in fluid communication with an insufflation port and configured to receive an insufflation medium therethrough and communicate the insufflation medium into contact with a colon of said patient;

a first retention portion coupled to a distal end portion of said body, said first retention portion configured to have a dimension transverse to an axis defined by said body sufficient to retain at least a portion of said body in the rectum, said first retention portion configured to be located in the rectum; and a seal disposed within the first passageway and configured to sealingly receive the medical tool of said body.

14. The apparatus of claim 13, further comprising:
an insufflation port coupled to said second passageway and configured to communicate said insufflation medium directly to said second passageway.

15. The apparatus of claim 13, further comprising:
a second retention portion coupled to a proximal end portion of said body, said second retention portion being inflatable and configured to be disposed outside of the patient's body.

16. An apparatus, comprising:
a body configured to be at least partially inserted into a rectum of a patient, the body having a proximal-most end configured to be disposed external to said patient, and a distal-most end configured to be received within said rectum of said patient, the body including:
a first passageway configured to sealingly pass a medical tool therethrough, and
a second passageway configured to communicate an insufflation medium therethrough so that the insufflation medium directly contacts the patient, said second passageway having a length between a proximal-most end of said second passageway and a distal-most end of said second passageway, said second passageway circumferentially surrounding and coaxial with said first passageway along the length of said second passageway wherein the first and second passageways are defined by a plurality of interior walls in the body, wherein each of the plurality of interior walls are fixed relative to one another; and a retention portion coupled to a distal end portion of said body, said retention portion configured to have a dimension transverse to an axis defined by said body sufficient to retain at least a portion of said body in the rectum, said retention portion configured to be located in the rectum.

17. The apparatus of claim 16, wherein said body is formed with a material such that said body conforms to an anus of the patient and provides a sealing fit between said body and the anus of the patient.

18. The apparatus of claim 16, further comprising:
an insufflation port coupled to said second passageway and configured to communicate said insufflation medium directly to said second passageway.

19. The apparatus of claim 16, wherein the retention portion is a first retention portion, the apparatus further comprising:
a second retention portion coupled to a proximal end portion of said body, said second retention portion being inflatable and configured to be disposed outside of the patient's body.

20. The apparatus of claim 16, wherein the insufflation medium is a pressurized liquid, the apparatus further comprising:
a source of pressurized liquid.

21. The apparatus of claim 20, further comprising a pressure relief valve coupled to said source of pressurized liquid.

22. The apparatus of claim 16, wherein said retention portion is inflatable.

23. The apparatus of claim 16, wherein said retention portion is at least one of substantially deformable and reconfigurable.

* * * * *

UNITED STATES PATENT AND TRADEMARK OFFICE
CERTIFICATE OF CORRECTION

PATENT NO. : 8,419,695 B2
APPLICATION NO. : 11/135428
DATED : April 16, 2013
INVENTOR(S) : Robert M. Rauker et al.

Page 1 of 1

It is certified that error appears in the above-identified patent and that said Letters Patent is hereby corrected as shown below:

In the Claims:

Claim 13, col. 11, line 14, "of said body" should be deleted.

Signed and Sealed this
Eighteenth Day of June, 2013

Teresa Stanek Rea
*Acting Director of the United States Patent and Trademark Office*